(12) United States Patent  
Kawasaki et al.

(10) Patent No.: US 8,553,996 B2
(45) Date of Patent: Oct. 8, 2013

(54) IMAGE TRANSMISSION TERMINAL

(75) Inventors: Shinya Kawasaki, Sagamihara (JP); Takemitsu Honda, Tokyo (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/271,787

(22) Filed: Oct. 12, 2011

(65) Prior Publication Data

US 2012/0082390 A1 Apr. 5, 2012

Related U.S. Application Data

(63) Continuation of application No. PCT/JP2010/002567, filed on Apr. 8, 2010.

(30) Foreign Application Priority Data

Apr. 13, 2009 (JP) .................................. 2009-097012

(51) Int. Cl.
*G06K 9/36* (2006.01)

(52) U.S. Cl.
USPC ................. 382/232; 382/275; 348/36; 348/65

(58) Field of Classification Search
USPC .............................. 382/232, 275; 348/36, 65
See application file for complete search history.

(56) References Cited

U.S. PATENT DOCUMENTS

| 2003/0177500 A1* | 9/2003 | Nakamura et al. ............. 725/105 |
| 2004/0030929 A1* | 2/2004 | Bi et al. ......................... 713/201 |
| 2006/0209185 A1* | 9/2006 | Yokoi ............................. 348/65 |
| 2007/0216781 A1 | 9/2007 | Miyanohara |

FOREIGN PATENT DOCUMENTS

| EP | 0979009 A2 | 2/2000 |
| EP | 2445210 A1 | 4/2012 |
| EP | 2478824 A1 | 7/2012 |
| JP | 6-335450 A | 12/1994 |
| JP | 10-294939 A | 11/1998 |
| JP | 2003-169291 A | 6/2003 |
| JP | 2003-274256 A | 9/2003 |

OTHER PUBLICATIONS

International Search Report of PCT/JP2010/002567, mailing date Jul. 20, 2010.

(Continued)

*Primary Examiner* — Chan S Park
*Assistant Examiner* — Eueng-Nan Yeh
(74) *Attorney, Agent, or Firm* — Westerman, Hattori, Daniels & Adrian, LLP

(57) ABSTRACT

The present invention is an image transmission terminal including: an image capture unit (17, 47) that outputs pixel signals; an image data generating unit (18, 48) that generates and outputs image frame data; a first image data compression unit (19, 49) that compresses and outputs the image frame data; a second image data compression unit (21, 51) that either leaves the image frame data uncompressed or else compresses and outputs the image frame data; an image selection unit (11, 13, 41, 43) that receives an operation input from a user, and selects the image frame data; an image data storage unit (22, 38, 52, 69) that stores the image frame data output from the second image data compression unit; and an image transmission unit (20, 50, 38) that wirelessly transmits the image frame data.

11 Claims, 10 Drawing Sheets

(56) References Cited

OTHER PUBLICATIONS

Extended European Search Report dated Nov. 30, 2012, issued in corresponding European patent application No. 10764235.7.

Japanese Office Action dated May 14, 2013, issued in corresponding Japanese Patent Application No. 2009-097012, w/ English translation (6 pages).

* cited by examiner though No. PCT/JP2010/002567, filed on

IMAGE TRANSMISSION TERMINAL

The present application is a Continuation Application of International Application No. PCT/JP2010/002567, filed on Apr. 8, 2010, claiming priority on Japanese Patent Application No. 2009-097012, filed on Apr. 13, 2009, the content of which is incorporated herein by reference in their entirety.

TECHNICAL FIELD

The present invention relates to an image transmission terminal that wirelessly transmits image data.

TECHNICAL BACKGROUND

In recent years, improvements have been made in the early discovery and diagnosis accuracy of lesioned portions by endoscopy. Moreover, a variety of treatment tools for use in an endoscope have been developed. As a result, even greater levels of performance are anticipated from endoscopes. However, image data for a body cavity interior which is captured by a conventional endoscope is transmitted by wire using an image transmission cable (referred to below as a 'cable') to a display apparatus set up at a location separated from the endoscope. Because of this, the positional relationships between a user, a test subject, and the display apparatus are limited by the cable.

Therefore, for example, in Japanese Unexamined Patent Application, First Publication No. H6-335450, an endoscope has been proposed in which image data captured by an endoscope is transmitted by wireless to a display apparatus. In this endoscope, there are no limits on the positional relationships between the user, the test subject, and the display apparatus, and neither are there any hindrances to the operation of the endoscope by the user.

Furthermore, in order to improve the early discovery and diagnosis accuracy of lesioned portions, further increases in image quality are sought in static image data which is photographed using an endoscope. As a consequence, there is a demand for static image data photographed by an endoscope to be either uncompressed data, or lossless compressed data in which absolutely no data loss is caused by the expansion processing, or lossy compressed data in which only slight data loss is caused by the expansion processing.

Furthermore, in moving image data, because the image frames are continuously updated, there is very little obvious deterioration in image quality. In contrast, in static image data in which the image frames are not updated, because the deterioration in image quality is obvious when a comparison with the same image frame is made, there is a demand for the quality of static image data to be higher than that of moving image data.

MEANS FOR SOLVING THE PROBLEM

An image transmission terminal of the present invention includes: an image capture unit that outputs pixel signals that correspond to an amount of light irradiated onto an imaging element; an image data generating unit that generates and then outputs image frame data based on the pixel signals; a first image data compression unit that compresses the image frame data at a predetermined compression rate and then outputs the image frame data; a second image data compression unit that either leaves the image frame data uncompressed or compresses the image frame data at a lower compression rate than the predetermined compression rate and then outputs the image frame data; an image selection unit that receives an operation input from a user, and that, based on the operation input, selects the image frame data captured by the image capture unit; an image data storage unit that, in accordance with the selection made by the image selection unit, stores the image frame data output from the second image data compression unit; and an image transmission unit that wirelessly transmits the image frame data output from the first image data compression unit.

In the image transmission terminal of the present invention, it is preferable for there to be provided an operating unit that receives a communication disconnection command operation performed by a user, and outputs an operation signal based on this operation, and for the image transmission unit to wirelessly transmit the image frame data stored in the image data storage unit when it receives the operation signal.

In the image transmission terminal of the present invention, when the image frame data is selected, it is preferable for the image selection unit to interrupt the wireless transmission of the image frame data output from the first image data compression unit, and to wirelessly transmit the image frame data stored in the image data storage unit.

In the image transmission terminal of the present invention, it is preferable for the image data storage unit to be a removable storage medium.

In the image transmission terminal of the present invention, it is preferable for the image data storage unit to be provided with an external interface.

In the image transmission terminal of the present invention, it is preferable for the image transmission terminal to wirelessly transmit the image frame data stored in the image data storage unit during a period when a wireless transmission of the image frame data output from the first image data compression unit has stopped.

In addition, as a result of the image transmission terminal wirelessly transmitting static image data that has a large data size during blank periods of the moving image transmission, a user is able to obtain high-quality static image data on a display apparatus.

BEST EMBODIMENTS FOR IMPLEMENTING THE INVENTION

First Embodiment

Figure 1:
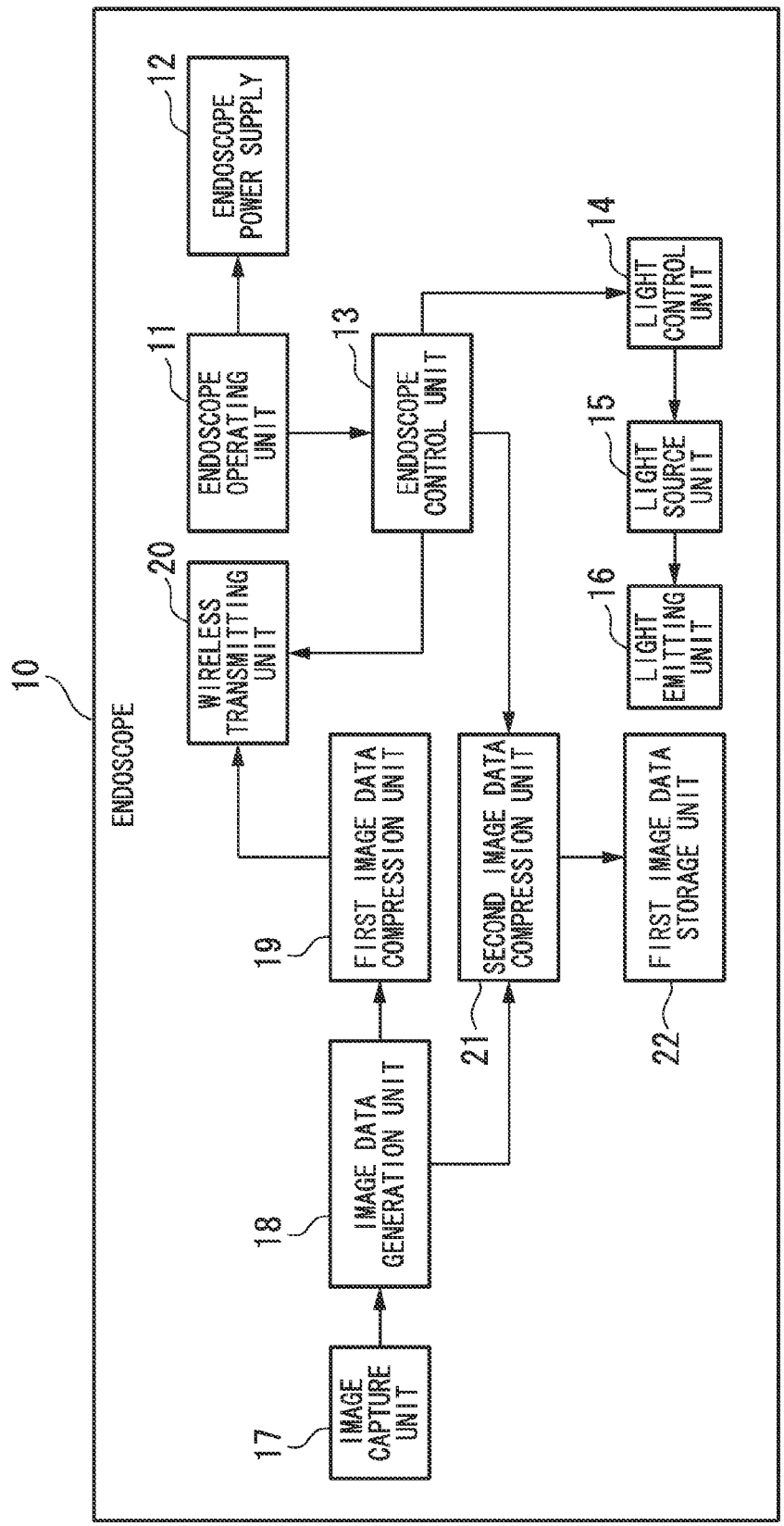
FIG. 1 is a block diagram of an endoscope according to an embodiment of the present invention.

Next, embodiments of the present invention will be described in detail with reference made to the drawings. FIG. 1 is a block diagram of an endoscope (i.e., an image transmission terminal) according to the present embodiment. In FIG. 1, an endoscope 10 is provided with an endoscope operating unit 11, an endoscope power supply 12, an endoscope control unit 13, a light control unit 14, a light source unit 15, a light emitting unit 16, an image capture unit 17, an image data generation unit 18, a first image data compression unit 19, a wireless transmitting unit 20, a second image data compression unit 21, and a first image data storage unit 22.

The endoscope operating unit 11 receives operation inputs from a user and outputs operation signals to the endoscope control unit 13 and the endoscope power supply 12. The endoscope power supply 12 receives a communication connection command from the endoscope operating unit 11 as an operation signal. When the endoscope power supply 12 receives a communication connection command, it begins supplying power to each block of the endoscope 10. The endoscope power supply 12 also receives a communication disconnection command from the endoscope operating unit 11 as an operation signal. When the endoscope power supply 12 receives a communication disconnection command, it stops supplying power to each block of the endoscope 10 after a predetermined length of time has elapsed since it received the communication disconnection command. Note that the timing at which the endoscope power supply 12 stops supplying power may also be supplied as a command from the endoscope control unit 13.

The endoscope control unit 13 receives light emission amount data for the light irradiated inside the body cavity as an operation signal from the endoscope operating unit 11, and outputs light emission amount data to the light control unit 14. When the endoscope control unit 13 receives a communication connection command from the endoscope operating unit 11 as an operation signal, it outputs to the wireless transmitting unit 20 a communication connection command to open communication with the wireless receiving unit 34 of the display apparatus 30 shown in FIG. 2 (described below). When, on the other hand, the endoscope control unit 13 receives a communication disconnection command as an operation signal from the endoscope operating unit 11, it outputs to the wireless transmitting unit 20 a communication disconnection command to close communication with the wireless receiving unit 34 of the display apparatus 30.

The endoscope control unit 13 receives a low (or non-) compression data generation command (for example, a static image photograph command) from the endoscope operating unit 11 as an operation signal, and outputs a low (or non-) compression data generation command to the second image data compression unit 21. Note that the endoscope control unit 13 may also be provided with a storage unit (not shown) for storing parameters used in program operations and the like.

The image capture unit 17 is provided with a solid state image sensor as typified by, for example, a CCD (Charge Coupled Device) image sensor (referred to below as a CCD), and a CMOS (Complementary Metal Oxide Semiconductor) image sensor (referred to below as a CMOS), and outputs to the image data generation unit 18 pixel signals that correspond to the amount of light irradiated onto the solid state image sensor. The image data generation unit 18 generates image frame data based on the pixel signals input from the image capture unit 17, and outputs image frame data to the first image data compression unit 19 and the second image data compression unit 21.

The first image data compression unit 19 performs intra-frame compression on the image frame data at a high compression ratio, and outputs the image frame data continuously as moving image data to the wireless transmitting unit 20.

When the wireless transmitting unit 20 receives a communication connection command from the endoscope control unit 13, it starts packet communication with the wireless receiving unit 34 of the display apparatus 30 shown in FIG. 2 (described below). The wireless transmitting unit 20 also executes modulation processing on the compressed image frame data input from the first image data compression unit 19, and transmits packet data for the image frame data as a wireless signal to the wireless receiving unit 34 of the display apparatus 30 shown in FIG. 2 (described below). In contrast, when the wireless transmitting unit 20 receives a communication disconnection command from the endoscope control unit 13, it ends the packet communication with the wireless receiving unit 34 of the display apparatus 30 shown in FIG. 2 (described below).

When the second image data compression unit 21 receives the low (or non-) compression data generation command from the endoscope control unit 13, it performs intra-frame compression at a low compression ratio on the image frame data, and then outputs the image frame data as static image data to the first image data storage unit 22. Here, when the image frame data is being extended, because this image frame data has a high image quality, the compressed image frame data which is output by the second image data compression unit 21 is low-compression data that has fewer data losses than the compressed image frame data output by the first image data compression unit 19. Note that the second image data compression unit 21 may output uncompressed data, or may output lossless compressed data in which absolutely no data loss is generated.

The first image data storage unit 22 receives compressed image frame data from the second image data compression unit 21 and stores this data. Note that the first image data storage unit 22 may, for example, be a removable storage medium such as a memory card. The first image data storage unit 22 may also be provided with an external interface (not shown), and after converting compressed image frame data into data that conforms to a communication standard for communicating with a peripheral device (not shown) of the endoscope 10, the first image data storage unit 22 may output the compressed image frame data to this peripheral device (not shown).

The light control unit 14 drives the light source unit 15 based on light emission amount data input from the endoscope control unit 13. The light source unit 15 is provided, for example, with a light emitting element such as an LED (Light Emitting Diode). Furthermore, in accordance with the drive signal from the light control unit 14, the light source unit 15 supplies light to the light emitting unit 16 via, for example, an optical fiber. The light emitting unit 16 irradiates light supplied in this manner to the interior of a body cavity.

Figure 2:
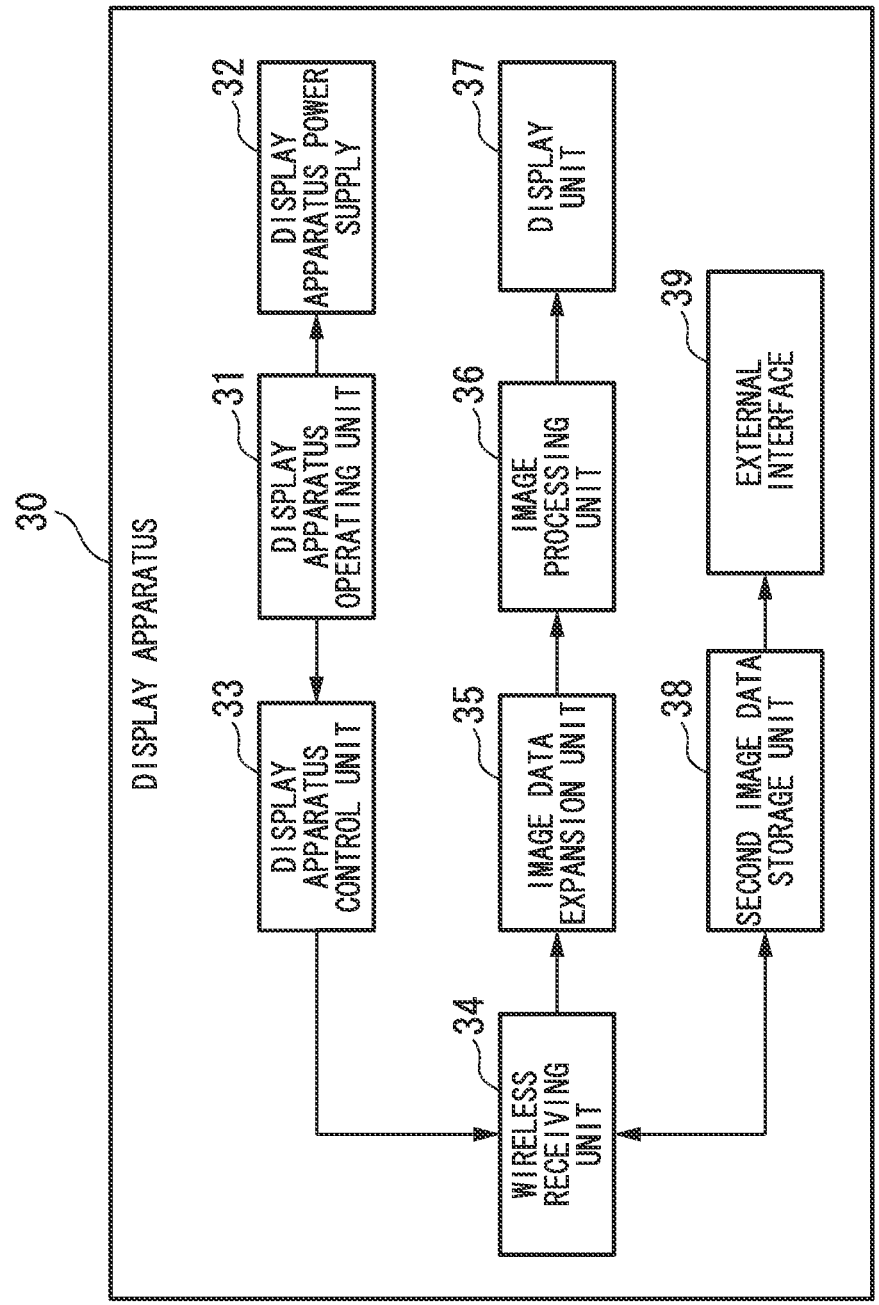
FIG. 2 is a block diagram of a display apparatus according to an embodiment of the present invention.

FIG. 2 is a block diagram of a display apparatus according to the present embodiment. A display apparatus 30 shown in FIG. 2 is provided with a display apparatus operating unit 31, a display apparatus power supply 32, a display apparatus control unit 33, a wireless receiving unit 34, an image data expansion unit 35, an image processing unit 36, a display unit 37, a second image data storage unit 38, and an external interface 39.

The display apparatus operating unit 31 receives operation inputs from a user, and outputs operation signals to the display apparatus control unit 33 and the display apparatus power supply 32. The display apparatus power supply 32 receives a communication connection command output from the display apparatus operating unit 31 as an operation signal. When the display apparatus power supply 32 receives the communication connection command, this display apparatus power supply 32 begins supplying power to each block of the display apparatus 30. The display apparatus power supply 32 also receives a communication disconnection command from the display apparatus operating unit 31 as an operation signal. When the display apparatus power supply 32 receives a communication disconnection command, this display apparatus power supply 32 stops supplying power to each block of the display apparatus 30 after a predetermined length of time has elapsed since it received the communication disconnection command. Note that the timing at which the display apparatus power supply 32 stops supplying power may also be supplied as a command from the display apparatus control unit 33.

When the display apparatus control unit 33 receives a communication connection command from the display apparatus operating unit 31 as an operation signal, it outputs to the wireless receiving unit 34 a communication connection command to open communication with the wireless transmitting unit 20 of the endoscope 10. When, on the other hand, the display apparatus control unit 33 receives a communication disconnection command from the display apparatus operating unit 31 as an operation signal, it outputs to the wireless receiving unit 34 a communication disconnection command to close communication with the wireless transmitting unit 20 of the endoscope 10.

When the wireless receiving unit 34 receives the communication connection command from the display apparatus control unit 33, it begins packet communication with the wireless transmitting unit 20 of the endoscope 10. In addition, the wireless receiving unit 34 also executes demodulation processing on the data received as a wireless signal from the endoscope 10, and acquires from the packet data the compressed image frame data transmitted from the wireless transmitting unit 20 of the endoscope 10, and outputs the compressed image frame data to the image data expansion unit 35 and the second image data storage unit 38. In contrast, when the wireless receiving unit 34 receives a communication disconnection command from the display unit control unit 33, it ends the packet communication with the wireless transmitting unit 20 of the endoscope 10.

The image data expansion unit 35 performs expansion processing on the compressed image frame data which is input, and outputs the result to the image processing unit 36. The image processing unit 36 performs image processing such as noise reduction and enhancement processing and the like on the expanded image frame data, and after the image frame data has completed the image processing, the image processing unit 36 outputs it to the display unit 37. The display unit 37 displays the image-processed image frame data as images on a display monitor or the like.

The second image data storage unit 38 stores compressed image frame data which is input from the wireless receiving unit 34. The external interface 39 acquires the compressed image frame data from the second image data storage unit 38, and after converting the compressed image frame data into data which conforms to the communication standard for communicating with the peripheral device (not shown) of the display apparatus 30, outputs the compressed image frame data to the peripheral device (not shown).

Figure 3:
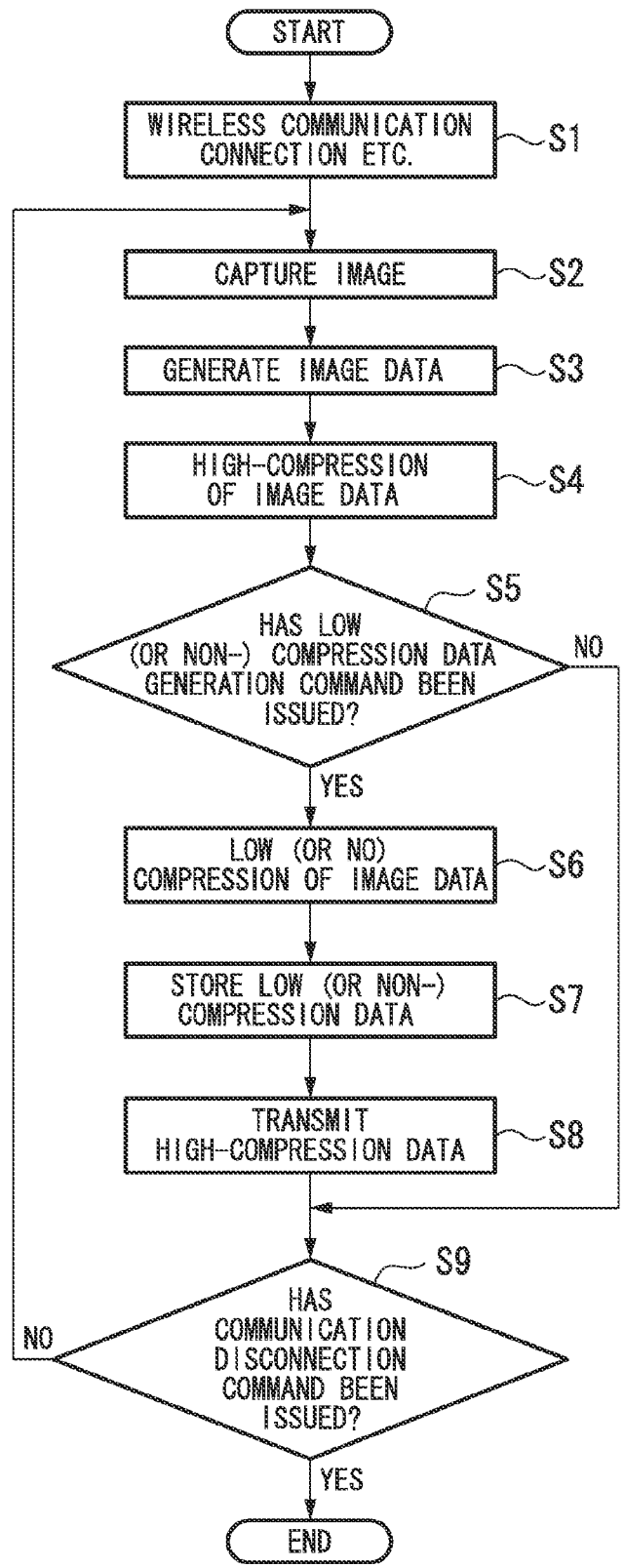
FIG. 3 is an operation flowchart of an endoscope according to an embodiment of the present invention.

FIG. 3 is an operation flowchart for the endoscope according to the present embodiment. The endoscope operating unit 11 receives operation inputs from a user, and outputs operation signals to the endoscope control unit 13 and the endoscope power supply 12. The endoscope power supply 12 receives a communication connection command from the endoscope operating unit 11 as an operation signal, and begins supplying power to each block of the endoscope 10.

The endoscope control unit 13 receives light emission amount data for the light irradiated inside the body cavity as an operation signal from the endoscope operating unit 11, and outputs the light emission amount data to the light control unit 14. The light control unit 14 drives the light source unit 15 based on light emission amount data input from the endoscope control unit 13. The light source unit 15 supplies light to the light emitting unit 16 via, for example, an optical fiber in accordance with the drive signal from the light control unit 14. The light emitting unit 16 irradiates light supplied in this manner to the interior of a body cavity.

The endoscope control unit 13 receives a communication connection command from the endoscope operating unit 11 as an operation signal, and outputs to the wireless transmitting unit 20 a communication connection command to open communication with the wireless receiving unit 34 of the display apparatus 30. The wireless transmitting unit 20 receives the communication connection command from the endoscope control unit 13, and begins packet communication with the wireless receiving unit 34 of the display apparatus 30 (step S1).

The image capture unit 17 to which power is being supplied outputs to the image data generation unit 18 pixel signals that correspond to the amount of light irradiated onto the solid state image sensor (step S2). The image data generation unit 18 generates image frame data based on the pixel signals input from the image capture unit 17, and outputs image frame data to the first image data compression unit 19 and the second image data compression unit 21 (step S3). The first image data compression unit 19 outputs the image frame data that has completed intra-frame compression to the wireless transmitting unit 20 (step S4).

The endoscope control unit 13 determines whether or not it has received a low (or non-) compression data generation command (for example, a static image photograph command) from the endoscope operating unit 11 (step S5). If the endoscope control unit 13 has not received a low (or non-) compression data generation command (for example, a static image photograph command) from the endoscope operating unit 11 as an operation signal, the routine moves to step S8.

If the endoscope control unit 13 has received a low (or non-) compression data generation command (for example, a static image photograph command) from the endoscope operating unit 11 as an operation signal, it outputs a low (or non-) compression data generation command to the second image data compression unit 21. When the second image data compression unit 21 receives the low (or non-) compression data generation command, it outputs to the first image data storage unit 22 the image frame data which has undergone intra-frame compression (step S6). The first image data storage unit 22 receives the image frame data which has undergone intra-frame compression (i.e., the low (or non-) compression data) from the second image data compression unit 21 and stores this data (step S7).

The wireless transmitting unit 20 executes modulation processing on the compressed image frame data (i.e., high-compression data) input from the first image data compression unit 19, and transmits packet data for the image frame data as a wireless signal to the wireless receiving unit 34 of the display apparatus 30 (step S8). When the wireless transmitting unit 20 receives a communication disconnection command, it ends the packet communication with the wireless receiving unit 34 of the display apparatus 30. If, on the other hand, the wireless transmitting unit 20 has not received a communication disconnection command, it returns to step S2. The endoscope power supply 12 determines whether or not it has received a communication disconnection command from the endoscope operating unit 11 as an operation signal. If the endoscope power supply 12 has received a communication disconnection command, it stops supplying power to each block of the endoscope 10 after a predetermined time has elapsed. If the endoscope power supply 12 has not received a communication disconnection command, it returns to step S2 (step S9).

Figure 4:
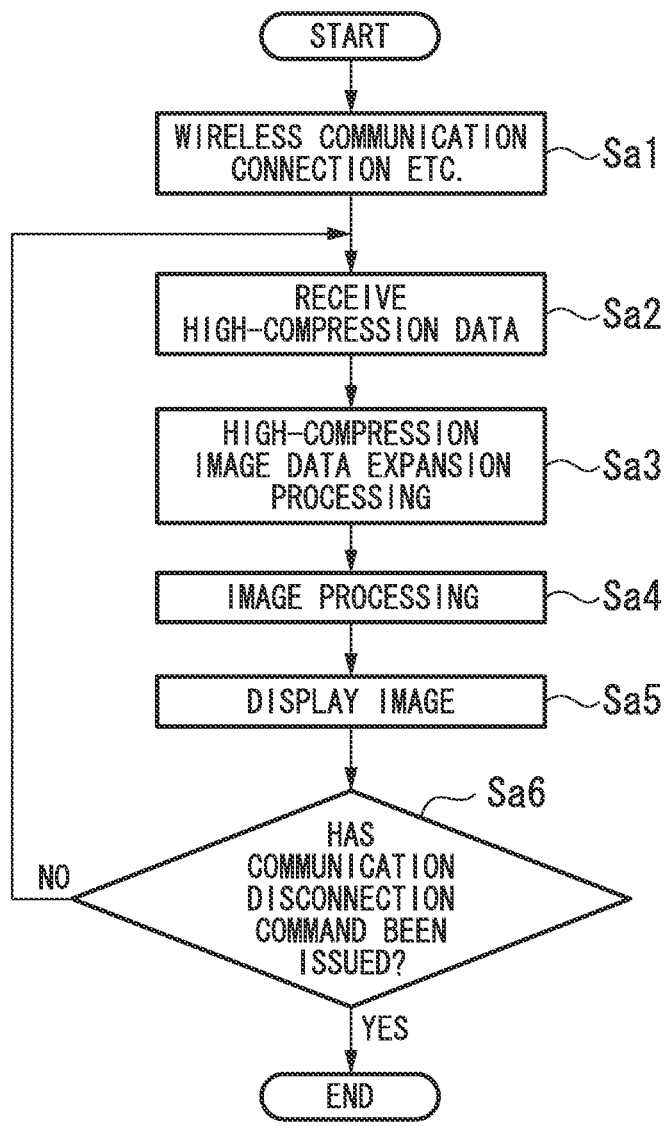
FIG. 4 is an operation flowchart of a display apparatus according to an embodiment of the present invention.

FIG. 4 is an operation flowchart for the display apparatus according to the present embodiment. The display apparatus operating unit 31 receives operating input from a user, and outputs operation signals to the display apparatus control unit 33 and the display apparatus power supply 32. The display apparatus power supply 32 receives a communication connection command from the display apparatus operating unit 31 as an operation signal, and starts supplying power to each block of the display apparatus 30.

The display apparatus control unit 33 receives the communication connection command from the display apparatus operating unit 31 as an operation signal, and outputs to the wireless receiving unit 34 a communication connection command instructing it to open communication with the wireless transmitting unit 20 of the endoscope 10. The wireless receiving unit 34 receives the communication connection command from the display apparatus control unit 33, and starts packet communication with the wireless transmitting unit 20 of the endoscope 10 (step Sa1).

The wireless receiving unit 34 performs the modulation processing on the data received as a wireless signal, and acquires from the packet data the compressed image frame data (i.e., high-compression data) transmitted from the wireless transmitting unit 20 of the endoscope 10, and outputs this to the image data expansion unit 35 and the second image data storage unit 38 (step Sa2). The image data expansion unit 35 performs expansion processing on the compressed image frame data (i.e., a high-compression data) which is input, and outputs the result to the image processing unit 36 (step Sa3). The image processing unit 36 performs image processing on the expanded image frame data, and outputs the image frame data before the image processing to the display unit 37 (step Sa4). The display unit 37 displays the image-processed image frame data as images on a display monitor or the like (step Sa5).

When the wireless receiving unit 34 receives a communication disconnection command, it ends the packet communication with the wireless transmitting unit 20 of the endoscope 10. If, on the other hand, the wireless receiving unit 34 has not received a communication disconnection command, it returns to step Sa2. The display apparatus power supply 32 determines whether or not it has received a communication disconnection command from the display apparatus operating unit 31 as an operation signal. If the display apparatus power supply 32 has received a communication disconnection command, it stops supplying power to each block of the display apparatus 30 after a predetermined time has elapsed. If the display apparatus power supply 32 has not received a communication disconnection command, it returns to step Sa2 (step Sa6).

If this type of method is employed, because the wireless transmitting unit 20 of the endoscope 10 does not wirelessly transmit low (or non-) compression data (for example, static image data) which has a large data size, the wireless transmitting unit 20 is able to wirelessly transmit high-compression data (for example, moving image data) to the display apparatus 30 without causing the communication speed to become insufficient. Moreover, because the endoscope 10 stores low (or non-) compression data which has a large data size in the first image data storage unit 22 which is provided in the endoscope 10, a user is able to obtain static image data having a high image quality in the endoscope 10. Furthermore, the user is able to display wirelessly transmitted moving image data on the display unit 37 of the display apparatus 30, and is able to obtain moving image data from the external interface 39 as well.

Note that it is also possible to employ a structure in which a low (or non-) compression data generation command (for example, a static image capture command) is transmitted from the wireless transmitting unit 20 of the endoscope 10 to the wireless receiving unit 34 of the display apparatus 30. By employing this structure, the display apparatus 30 which receives the low (or non-) compression data generation command stages a viewing display in which the updating of the image frame data (for example, moving image data) currently displayed on the display unit 37 is temporarily halted. By staging this type of viewing display, the endoscope 10 is able to notify the user that the low (or non-) compression data generation processing has been executed.

Second Embodiment

Figure 5:
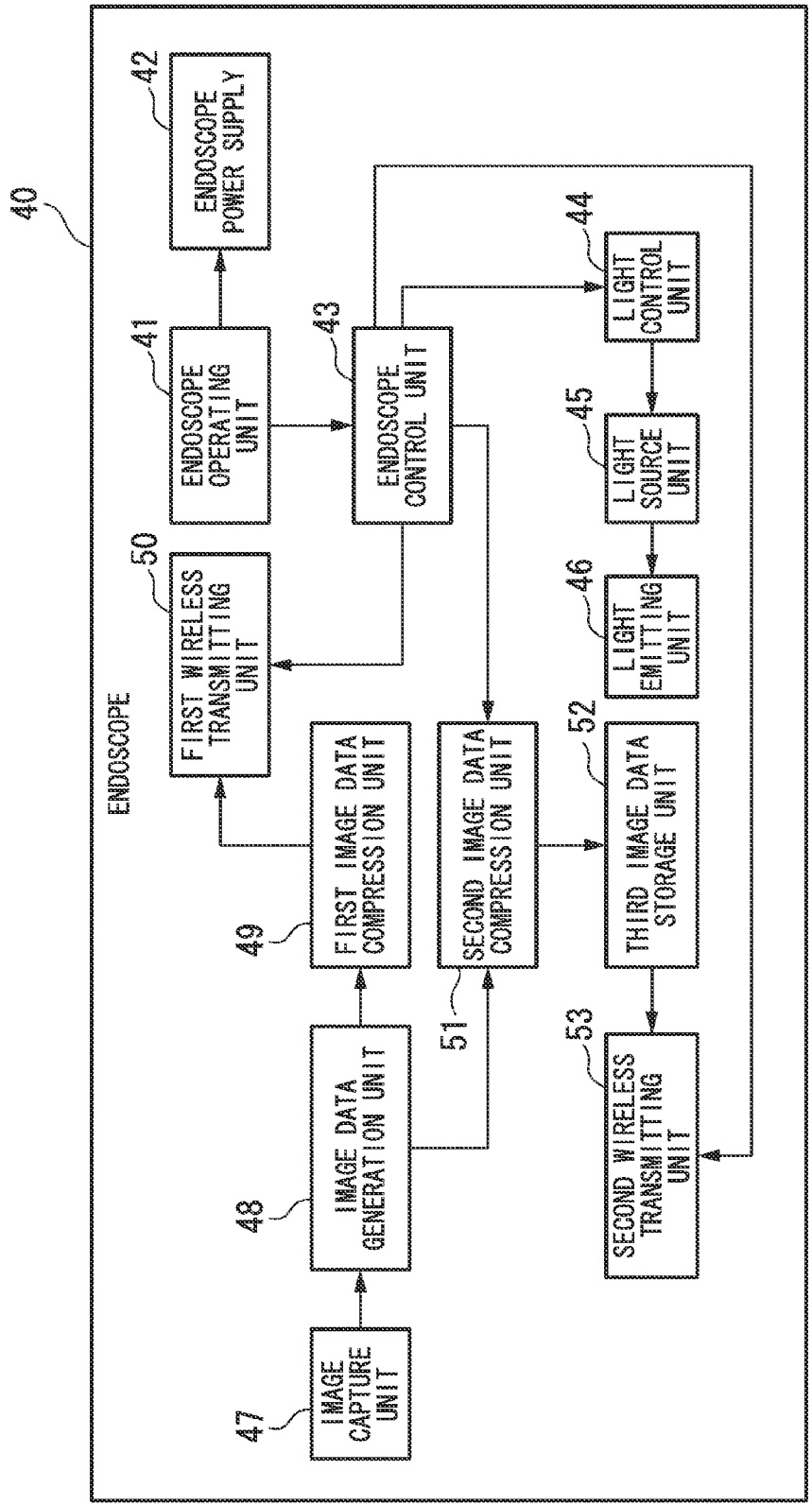
FIG. 5 is a block diagram of an endoscope according to an embodiment of the present invention.

Next, a second embodiment of the present invention will be described. FIG. 5 is a block diagram of an endoscope according to the present embodiment. In FIG. 5, an endoscope 40 is provided with an endoscope operating unit 41, an endoscope power supply 42, an endoscope control unit 43, a light control unit 44, a light source unit 45, a light emitting unit 46, an image capture unit 47, an image data generation unit 48, a first image data compression unit 49, a first wireless transmitting unit 50, a second image data compression unit 51, a third image data storage unit 52, and a second wireless transmitting unit 53.

The endoscope operating unit 41 performs the same type of operations as the endoscope operating unit 11 shown in FIG. 1. The endoscope power supply 42 performs the same type of operations as the endoscope power supply 12 shown in FIG. 1. The endoscope control unit 43 performs the same type of operations as the endoscope control unit 13 shown in FIG. 1. The endoscope control unit 43 outputs to the first wireless transmitting unit 50 a communication connection command to open communication with the first wireless receiving unit 64 of the display apparatus 60 shown in FIG. 6 (described below). In the same way, the endoscope control unit 43 outputs to the second wireless transmitting unit 53 a communication connection command to open communication with the second wireless receiving unit 68 of the display apparatus 60 shown in FIG. 6 (described below). The endoscope control unit 43 receives a communication connection command for the endoscope 40 from the endoscope operating unit 41 as an operation signal. Communication disconnection commands are executed by the endoscope control unit 43 operating in the same way as the endoscope control unit 13 shown in FIG. 1.

The endoscope control unit 43 issues commands about packet data transmission timings to the first wireless transmitting unit 50 and the second wireless transmitting unit 53. The endoscope control unit 43 also acquires from the first wireless transmitting unit 50 information showing whether or not the first wireless transmitting unit 50 has completed the packet data transmission. In the same way, the endoscope control unit 43 acquires from the second wireless transmitting unit 53 information showing whether or not the second wireless transmitting unit 53 has completed the packet data transmission.

When the endoscope control unit 43 has received a low (non-) compression data generation command (for example, a command to photograph a static image) as an operation signal from the endoscope operating unit 41, it outputs the low (non-) compression data generation command to the second image data compression unit 51. Furthermore, the endoscope control unit 43 also commands the first wireless transmitting unit 50 to attach "high-compression data storage command information" to the image frame data. Here, this "high-compression data storage command information" refers to information referenced by the first wireless receiving unit 64 of the display apparatus 60 in order store image frame data transmitted from the first wireless transmitting unit 50 in the fourth image data storage unit 69 of the display apparatus 60 shown in FIG. 6 (described below). Note that this "high-compression data storage command information" is not only information attached to image frame data, but may also be information originally included in the image frame data. Furthermore, it is also possible to switch the bits showing this "high-compression data storage command information" between "valid" and "invalid".

The endoscope control unit 43 which has received this low (non-) compression data generation command may also command the first wireless transmitting unit 50 such that the first wireless transmitting unit 50 temporarily halts the packet data transmission until the packet data transmission of the second wireless transmitting unit 53 is completed. By doing this, packet data is transmitted to the second wireless transmitting unit 53 while the packet data transmission performed by the first wireless transmitting unit 50 is temporarily halted.

The light control unit 44, the light source unit 45, and the light emitting unit 46 perform the same type of operations respectively as the light control unit 14, the light source unit 15, and the light emitting unit 16 in FIG. 1. The image capture unit 47 performs the same type of operations as the image capture unit 17 in FIG. 1. The image data generation unit 48 performs the same type of operations as the image data generation unit 18 in FIG. 1.

The first image data compression unit 49 performs the same type of operations as the first image data compression unit 19 in FIG. 1. The first image data compression unit 49 outputs image frame data (for example, moving image data) that has undergone intra-frame compression to the first wireless transmitting unit 50.

The first wireless transmitting unit 50 performs the same type of operations as the first wireless transmitting unit 20. The first wireless transmitting unit 50 transmits packet data for the image frame data as a wireless signal to the first wireless receiving unit 64 of the display apparatus 60 shown in FIG. 6 (described below). Moreover, when the first wireless transmitting unit 50 receives a command to attach "high-compression data storage command information" from the endoscope control unit 43, it transmits the packet data after attaching the "high-compression data storage command information" to the image frame data.

The second image data compression unit 51 performs the same type of operations as the second image data compression unit 21 in FIG. 1. The second image data compression unit 51 outputs to the third image data storage unit 52 image frame data (for example, static image data) that has undergone intra-frame compression. Here, because this image frame data is high image quality data, even after the image frame data has been expanded, the compressed image frame data output by the second image data compression unit 51 is low-compression data having fewer data losses than the compressed image frame data output by the first image data compression unit 49. Note that it is also possible for the second image data compression unit 51 to output non-compression data. Alternatively, the second image data compression unit 51 may output lossless compressed data in which absolutely no data losses are generated by the expansion processing.

The third image data storage unit 52 corresponds to the first image data storage unit 22 in FIG. 1, and receives compressed image frame data from the second image data compression unit 51 and stores it. The third image data storage unit 52 also outputs compressed image frame data to the second wireless transmitting unit 53.

When the second wireless transmitting unit 53 received a communication connection command from the endoscope control unit 43, it starts packet communication with the second wireless receiving unit 68 of the display apparatus 60 shown in FIG. 6 (described below). The second wireless transmitting unit 53 also transmits data packets of the image frame data as a wireless signal to the second wireless receiving unit 68 of the display apparatus 60 shown in FIG. 6 (described below). On the other hand, when the second wireless transmitting unit 53 receives a communication disconnection command from the endoscope control unit 43, it ends the packet communication with the second wireless receiving unit 68 of the display apparatus 60 shown in FIG. 6 (described below).

Note that it is not necessary for the second wireless transmitting unit 53 to employ the same communication system as the first wireless transmitting unit 50, and it is also possible for it to execute faster communication than the first wireless transmitting unit 50. For example, it is also possible for the second wireless transmitting unit 53 to perform multi-value modulation in which a large quantity of information is delivered in one segment (symbol) of a signal. It is also possible for the second wireless transmitting unit 53 to have a wider communication bandwidth than the first wireless transmitting unit 50.

Figure 6:
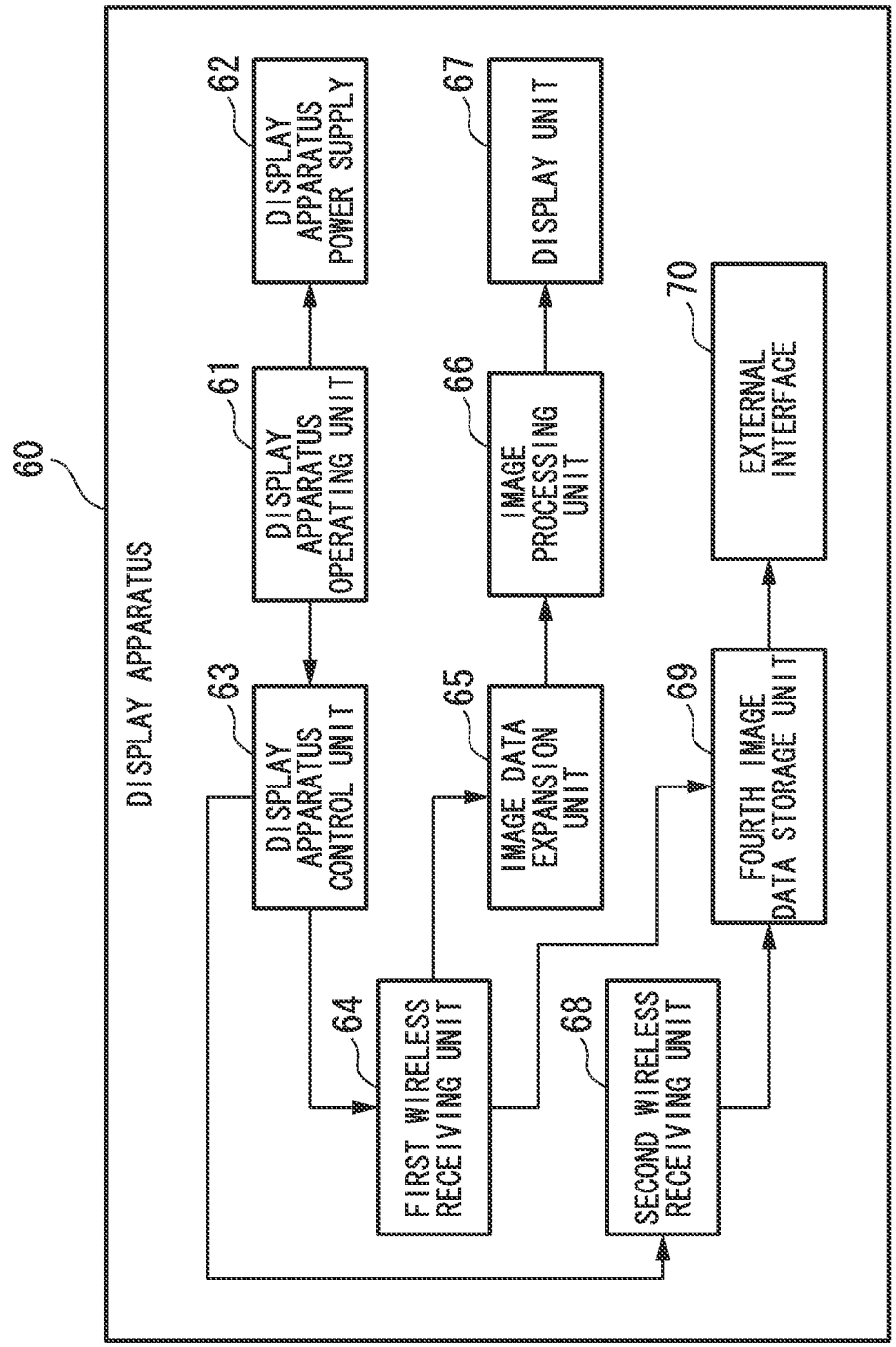
FIG. 6 is a block diagram of a display apparatus according to an embodiment of the present invention.

FIG. 6 is a block diagram of a display apparatus according to the present embodiment. A display apparatus 60 shown in FIG. 6 is provided with a display apparatus operating unit 61, a display apparatus power supply 62, a display apparatus control unit 63, a first wireless receiving unit 64, an image data expansion unit 65, an image processing unit 66, a display unit 67, a second wireless receiving unit 68, a fourth image data storage unit 69, and an external interface 70.

The display apparatus operating unit 61 performs the same type of operations as the display apparatus operating unit 31 in FIG. 2. The display apparatus power supply 62 performs the same type of operations as the display apparatus power supply 32 in FIG. 1. The display apparatus control unit 63 performs the same type of operations as the display apparatus control unit 33 in FIG. 2. The display apparatus control unit 63 receives a communication connection command as an operation signal from the display apparatus operating unit 61, and outputs to the first wireless receiving unit 64 a communication connection command to open communication with the first wireless transmitting unit 50 of the endoscope 40. In the same way, the display apparatus control unit 63 outputs to the second wireless receiving unit 68 a communication connection command to open communication with the second wireless transmitting unit 53 of the endoscope 40. Communication disconnection commands are executed by the display apparatus control unit 63 operating in the same way as the endoscope control unit 33 shown in FIG. 2.

The first wireless receiving unit 64 receives a communication connection command from the display apparatus control unit 63, and starts packet communication with the first wireless transmitting unit 50 of the endoscope 40. The first wireless receiving unit 64 performs demodulation processing on the data received as a wireless signal, and acquires compressed image frame data transmitted from the first wireless transmitting unit 50 of the endoscope 40 from the packet data, and then outputs this to the image data expansion unit 65.

The first wireless receiving unit 64 detects whether or not "high-compression data storage command information" is attached to the image frame data (i.e., high-compression data) transmitted from the first wireless transmitting unit 50 in FIG. 5. If this "high-compression data storage command information" is attached, the first wireless receiving unit 64 outputs the compressed image frame data to the fourth image data storage unit 69 as well.

The second wireless receiving unit 68 receives a communication connection command from the display apparatus control unit 63, and starts packet communication with the second wireless transmitting unit 53 of the endoscope 40. The second wireless receiving unit 68 executes demodulation processing on the data received as a wireless signal, and acquires compressed image frame data transmitted from the second wireless transmitting unit 53 of the endoscope 40 from the packet data, and then outputs this to the fourth image data storage unit 69.

The image data expansion unit 65 performs expansion processing on the compressed image frame data which is input into it, and then outputs the results to the image processing unit 66. The image processing unit 66 performs image processing such as noise reduction and enhancement processing and the like on the expanded image frame data, and after the image frame data has completed the image processing, the image processing unit 66 outputs it to the display unit 67. The display unit 67 displays the image-processed image frame data as images on a display monitor or the like.

The fourth image data storage unit 69 stores compressed image frame data which is input into it. Note that the fourth image data storage unit 69 may also be a removable storage medium as typified, for example, by memory cards. The external interface 70 acquires the compressed image frame data from the fourth image data storage unit 69, and after converting it into data which conforms to the communication standard for communicating with the peripheral device (not shown) of the display apparatus 60, outputs the compressed image frame data to the peripheral device (not shown).

Figure 7:
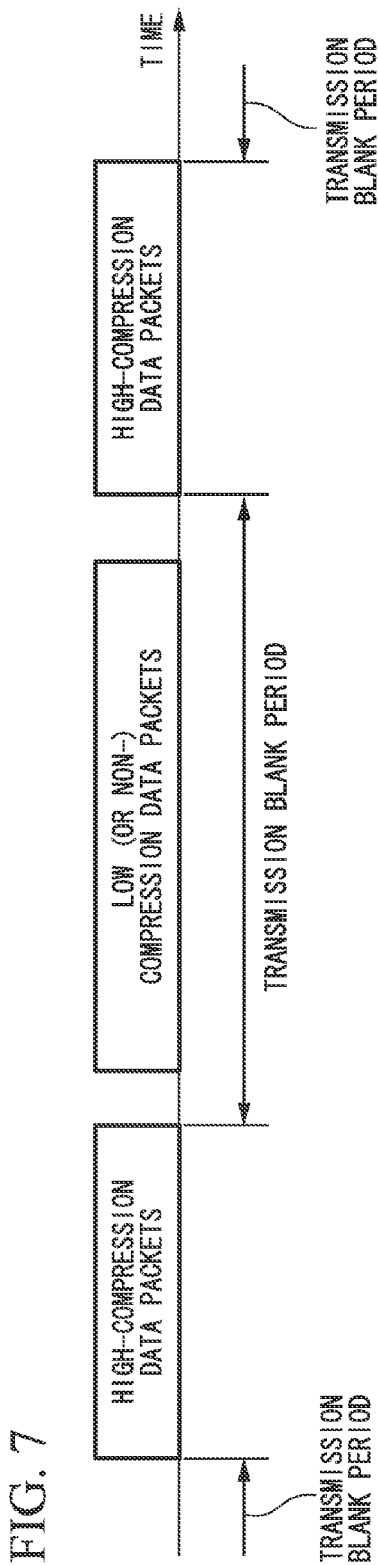
FIG. 7 is a view showing the packet data transmission timings of a first wireless transmitting unit 50 and the packet data transmission timings of a second wireless transmitting unit 53.

FIG. 7 shows the packet data transmission timings of the first wireless transmitting unit 50 and the packet data transmission timings of the second wireless transmitting unit 53. The first wireless transmitting unit 50 transmits high-compression data packets (for example, moving image data). The second wireless transmitting unit 53 transmits low (or non-) compression data packets (for example, static image data). Here, it is also possible for the endoscope control unit 43 to decide transmission blank periods, which are periods during which the first wireless transmitting unit 50 is not transmitting packet data, for example, by determining whether or not the image frame data transmission is fully completed. Alternatively, these transmission blank periods may also be decided by the packet data being transmitted at a predetermined cycle. Note that it is also possible for the first wireless transmitting unit 50 and the second wireless transmitting unit 53 to transmit packet data alternatingly at a predetermined cycle regardless of whether they have received commands from the endoscope control unit 43.

Figure 8:
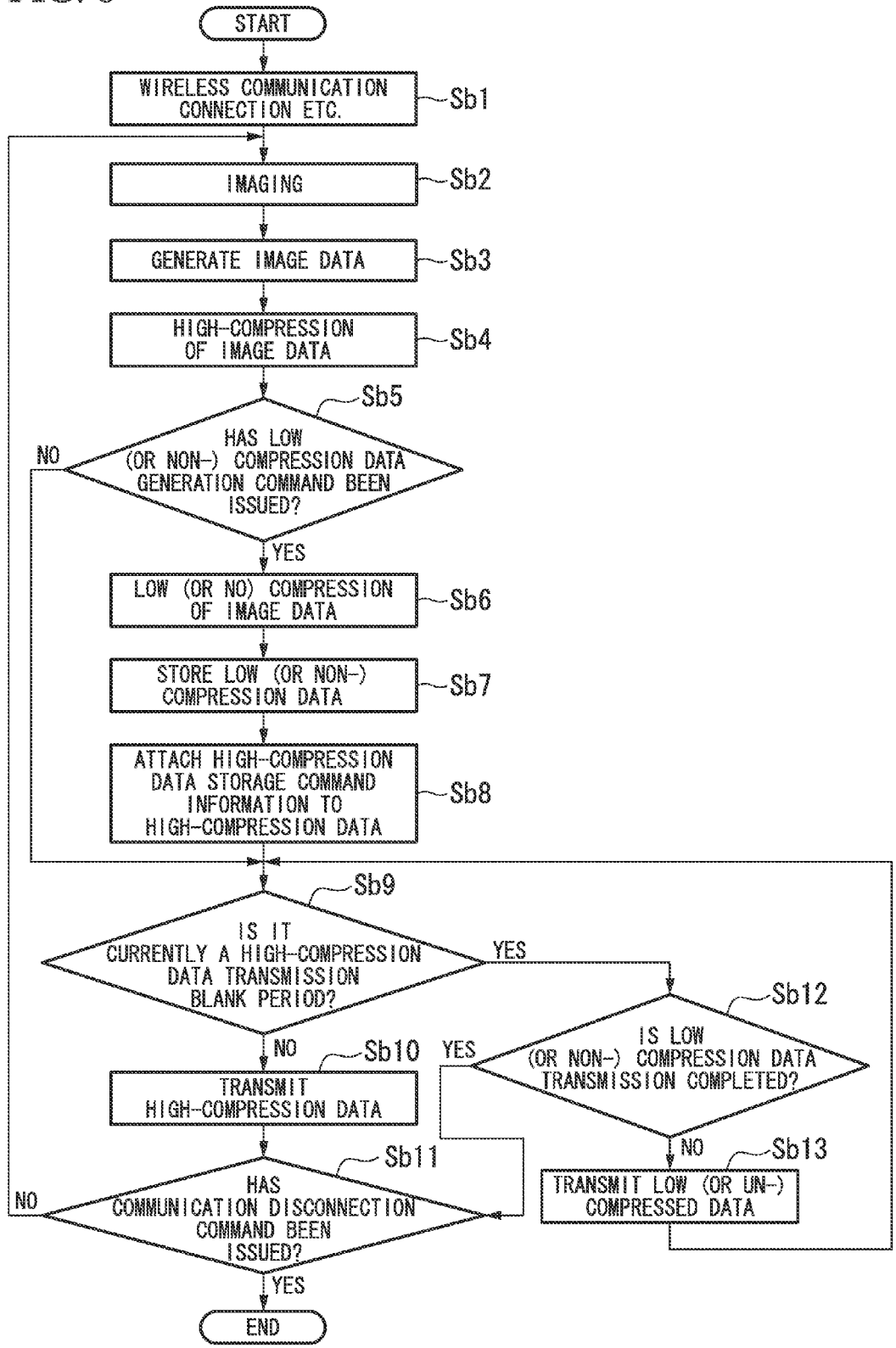
FIG. 8 is an operation flowchart of an endoscope according to an embodiment of the present invention.

FIG. 8 is an operation flowchart of the endoscope according to the present embodiment. The endoscope operating unit 41 receives operation inputs from a user, and outputs operation signals to the endoscope control unit 43 and the endoscope power supply 42. The endoscope power supply 42 receives a communication connection command from the endoscope operating unit 41 as an operation signal, and begins supplying power to each block of the endoscope 40.

The endoscope control unit 43 receives light emission amount data for the light irradiated inside the body cavity as an operation signal from the endoscope operating unit 41, and outputs the light emission amount data to the light control unit 44. The light control unit 44 drives the light source unit 45 based on light emission amount data input from the endoscope control unit 43. The light source unit 45 supplies light to the light emitting unit 46 via, for example, an optical fiber in accordance with the drive signal from the light control unit 44. The light emitting unit 46 irradiates light supplied in this manner to the interior of a body cavity.

The endoscope control unit 43 receives a communication connection command from the endoscope operating unit 41 as an operation signal. The endoscope control unit 43 outputs to the first wireless transmitting unit 50 a communication connection command to open communication with the first wireless receiving unit 64 of the display apparatus 60. The first wireless transmitting unit 50 receives the communication connection command from the endoscope control unit 43, and begins packet communication with the first wireless receiving unit 64 of the display apparatus 60. In the same way, the second wireless transmitting unit 53 begins packet communication with the second wireless receiving unit 68 of the display apparatus 60 (step Sb1).

The routine from step Sb2 to step Sb3 is the same as the routine from step S2 to step S3 in FIG. 3. The first image data compression unit 49 outputs to the first wireless transmitting unit 50 the image frame data that has completed intra-frame compression (step Sb4).

The endoscope control unit 43 determines whether or not a low (or non-) compression data generation command has been received from the endoscope operating unit 41 (step Sb5). If the endoscope control unit 43 has received a low (or non-) compression data generation command (for example, a static image capture command) as an operation signal from the endoscope operating section 41, it outputs the low (or non-) compression data generation command to the second image data compression unit 51. Furthermore, the endoscope control unit 43 also commands the first wireless transmitting unit 50 to attach "high-compression data storage command information" to the image frame data (i.e., high-compression data) output by the first image data compression unit 49. If a low (or non-) compression data generation command has not been received as an operation signal from the endoscope operating section 41, the endoscope control unit 43 moves to step Sb9.

When the second image data compression unit 51 receives the low (or non-) compression data generation command, it outputs the compressed image frame data to the third image data storage unit 52 (step Sb6). The third image data storage unit 52 receives the compressed image frame data from the second image data compression unit 51 and stores this data (step Sb7). The first wireless transmitting unit 50 which was commanded to attach the "high-compression data storage command information" attaches the "high-compression data storage commands information" to the high-compression data (step Sb8).

Next, the endoscope control unit 43 determines whether or not there is currently a transmission blank period in accordance with the aforementioned conditions (step Sb9). If it is not determined to be a transmission blank period, the endoscope control unit 43 commands the first wireless transmitting unit 50 to transmit packet data. The first wireless transmitting unit 50 then transmits data packets of the image frame data (i.e., high-compression data) as a wireless signal to the first wireless receiving unit 64 of the display apparatus 60 (step Sb10).

When the first wireless transmitting unit 50 and the second wireless transmitting unit 53 receive a communication disconnection commands, they end packet communication with the respective wireless receiving units of the display apparatus 60. In contrast, if they have not received a communication disconnection command, the first wireless transmitting unit 50 and the second wireless transmitting unit 53 return to step Sb2. The endoscope power supply 42 also determines whether or not a communication disconnection command has been received as an operation signal from the endoscope operating unit 41. If a communication disconnection command has been received, the endoscope power supply 42 stops supplying power to each block of the endoscope 40 after a predetermined time has elapsed. If a communication disconnection command has not been received, the endoscope power supply 42 returns to step Sb2 (Step Sb11).

If it is determined in step Sb9 to be a transmission blank period, the endoscope control unit 43 determines whether or not the packet data transmission by the second wireless transmitting unit 53 was completed during the previous attempt. If the transmission was completed, the routine returns to step Sb11 (step Sb12). If the transmission was not completed, the endoscope control unit 43 commands the second wireless transmitting unit 53 to transmit packet data. The second wireless transmitting unit 53 then transmits data packets of the image frame data (i.e., low (or un-) compressed data) as a wireless signal to the second wireless receiving unit 68, and the routine moves to step Sb9 (step Sb13).

Figure 9:
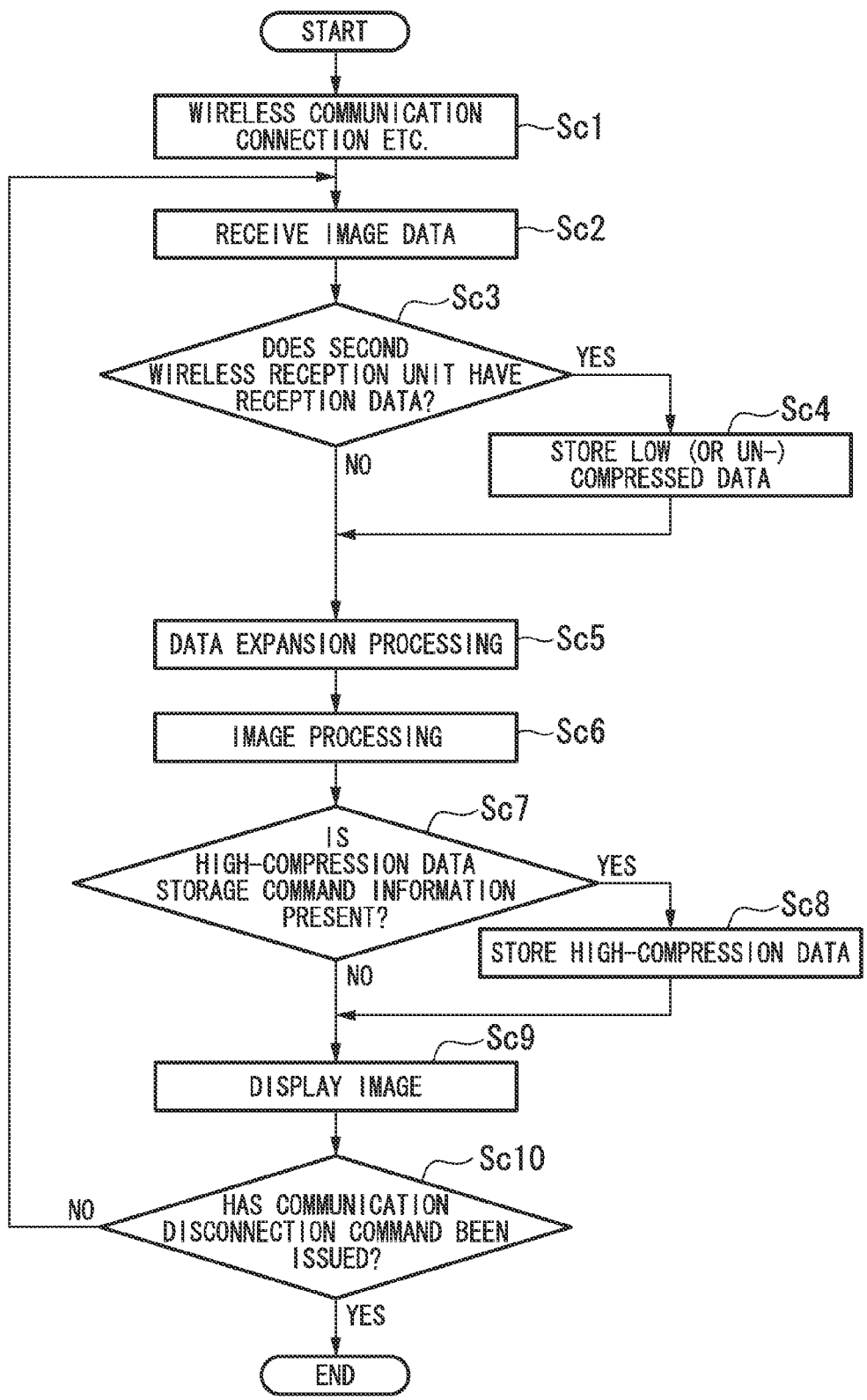
FIG. 9 is an operation flowchart of a display apparatus according to an embodiment of the present invention.

FIG. 9 is an operation flowchart for the display apparatus according to the present embodiment. The display apparatus operating unit 61 receives operating input from a user, and outputs operation signals to the display apparatus control unit 63 and the display apparatus power supply 62. The display apparatus power supply 62 receives a communication connection command from the display apparatus operating unit 61 as an operation signal, and starts supplying power to each block of the display apparatus 60.

The display apparatus control unit 63 receives the communication connection command from the display apparatus operating unit 61 as an operation signal, and outputs to the first wireless receiving unit 64 a communication connection command instructing it to open communication with the wireless transmitting unit 50 of the endoscope 40. The first wireless receiving unit 64 receives the communication connection command from the display apparatus control unit 63, and starts packet communication with the first wireless transmitting unit 50 of the endoscope 40. In the same way, the second wireless receiving unit 68 receives the communication connection command from the display apparatus control unit 63, and starts packet communication with the second wireless transmitting unit 53 of the endoscope 40 (step Sc1).

If a packet data transmission has been made from the first wireless transmitting unit 50, the first wireless receiving unit 64 executes demodulation processing on the received data, and acquires the packet data from the compressed image frame data, and then outputs it to the image data expansion unit 65 (step Sc2). In step Sc3, if a transmission of packet data has been made from the second wireless transmitting unit 53, the second wireless receiving unit 68 executes demodulation processing on the received data, and acquires the packet data from the compressed image frame data, and then outputs it to the image data expansion unit 65 and the fourth image data storage unit 69. The fourth image data storage unit 69 stores the compressed image frame data (i.e., low (or un-) compressed data) (step Sc4).

The image data expansion unit 65 performs expansion processing using a plurality of packets of packet data. Accordingly, even if packet data was not received in step Sc2, the image data expansion unit 65 executes expansion processing on the compressed image frame data that has been input up until the previous time (step Sc5). The image processing unit 66 executes image processing on the expanded image frame data, and outputs the image frame data which has completed image processing to the display unit 67 (step Sc6).

The first wireless receiving unit 64 detects whether or not "high-compression data storage command information" is attached to the image frame data in the received packet data (step Sc7). If this "high-compression data storage command information" is attached, the first wireless receiving unit 64 outputs the compressed image frame data to the fourth image data storage unit 69. The fourth image data storage unit 69 stores the compressed image frame data (step Sc8).

The display unit 67 displays the image-processed image frame data as images on a display monitor or the like (step Sc9). When the first wireless receiving unit 64 and the second wireless receiving unit 68 receive a communication disconnection command, they end the packet communication with the respective wireless transmitting units of the endoscope 40. If, on the other hand, the first wireless receiving unit 64 and the second wireless receiving unit 68 have not received a communication disconnection command, they return to step Sc2. The display apparatus power supply 62 determines whether or not it has received a communication disconnection command from the display apparatus operating unit 61 as an operation signal. If the display apparatus power supply 62 has received a communication disconnection command, it stops supplying power to each block of the display apparatus 60 after a predetermined time has elapsed. If the display apparatus power supply 62 has not received a communication disconnection command, it returns to step Sc2 (step Sc10).

If this type of method is employed, the second wireless transmitting unit 53 of the endoscope 40 is able to wirelessly transmit low (or non-) compression data (for example, static image data) which has a large data size during blank periods of high-compression data (for example, moving image data) transmission. Namely, the first wireless transmitting unit 50 is able to wirelessly transmit high-compression data to the display apparatus 60 without causing the communication speed to become insufficient. As a result, the user is able to obtain static image data having a high image quality from the fourth image data storage unit 69 and the external interface 70 of the display apparatus 60.

Figure 10:
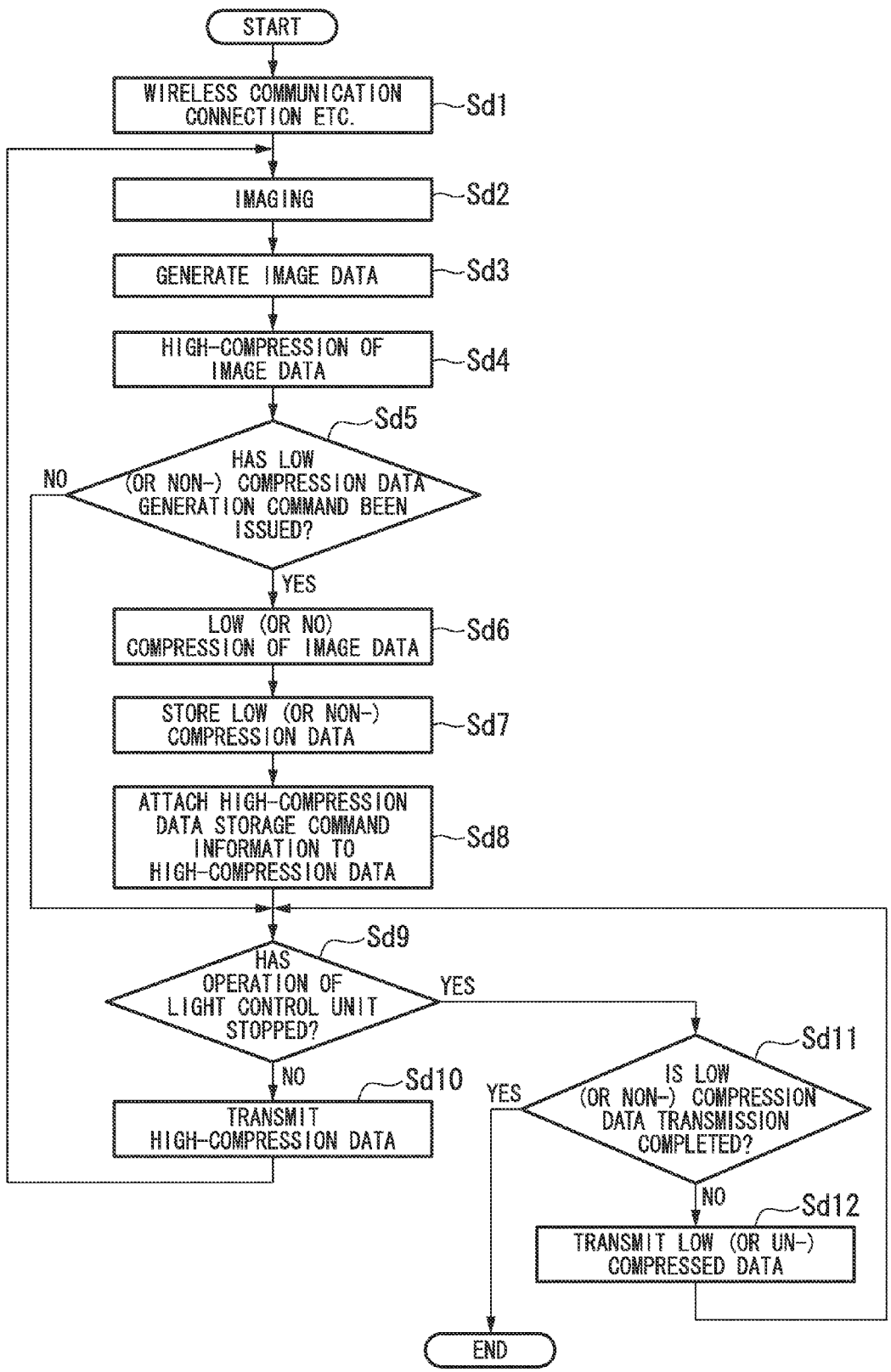
FIG. 10 is an operation flowchart of a display apparatus according to an embodiment of the present invention.

Note that the timings of the low (or non-) compression data (for example, static image data) transmissions may also be set in the following manner. FIG. 10 is an operation flowchart of the display apparatus according to the present embodiment. Here, step Sd1 through step Sd8 are the same as step Sb1 through step Sb8 in FIG. 8.

When a user wishes to end an examination being performed with the endoscope 40, the endoscope operating unit 41 receives a stop command for the light control unit 44 (i.e., a command to turn off the light emitting unit 46), and notifies the endoscope control unit 43 about the stop command for the light control unit 44. The endoscope control unit 43 determines whether or not it has received a stop command for the light control unit 44 from the endoscope operating unit 41

(step Sd9). If the endoscope control unit 43 has not received the stop command for the light control unit 44, then because it assumes that the user is continuing the examination performed with the endoscope 40, the endoscope control unit 43 commands the first wireless transmitting unit 50 to transmit data packets of the image frame data (i.e., high-compression data). The first wireless transmitting unit 50 transmits data packets of the image frame data (i.e., a high-compression data) as a wireless signal to the first wireless receiving unit 64 of the display apparatus 60, and then moves to step Sd2 (step Sd10).

When the endoscope control unit 43 has received a stop command for the light control unit 44, then because it assumes that the user is ending the examination performed with the endoscope 40, the endoscope control unit 43 receives the stop command for the light control unit 44 and stops operations of the light control unit 44. In addition, the endoscope control unit 43 commands the first wireless transmitting unit 50 to stop transmitting image frame data. Furthermore, the endoscope control unit 43 determines whether or not the second wireless transmitting unit 53 has completed the transmission of the entire group of data packets. If the transmission has not been completed, the endoscope control unit 43 commands the second wireless transmitting unit 53 to transmit the un-transmitted packet data. When the second wireless transmitting unit 53 receives the packet data transmission command, it transmits the data packets of image frame data (i.e., low (or un-) compressed data) as a wireless signal to the second wireless receiving unit 68 of the display apparatus 60, and then moves to step Sd9 (step Sd12).

If this type of method is employed, because the second wireless transmitting unit 53 of the endoscope 40 wirelessly transmits low (or non-) compression data (for example, static image data) which has a large data size collectively after the transmission of the high-compression data (for example, moving image data) has been stopped, the first wireless transmitting unit 50 is able to wirelessly transmit high-compression data to the display apparatus 60 without causing the communication speed to become insufficient. As a result, the user is able to obtain static image data having a high image quality from the fourth image data storage unit 69 and the external interface 70 of the display apparatus 60.

Note that for the determination conditions of step Sd9 in FIG. 10, instead of determining whether or not a stop command for the light control unit 44 has been received, it is also possible to determine whether or not a communication disconnection command has been made to the endoscope power supply 42, namely, whether the endoscope power supply 42 has received a command to stop supplying power to the endoscope 40. Furthermore, if the power held by the endoscope power supply 42 is insufficient, then it is also possible for the endoscope 40 to wait until the endoscope power supply 42 has been recharged, and to then use the next power supply command as a trigger for collectively transmitting data packets to the display apparatus 60.

Embodiments of this invention have been described above in detail with reference made to the drawings. However, the specific structure thereof is not limited to these embodiments, and various design modifications and the like are included therein insofar as they do not depart from the spirit or scope of this invention.

Moreover, the image capture unit described in the present invention corresponds to the image capture unit 17 and the image capture unit 47. The image data generation unit corresponds to the image data generation unit 18 and the image data generation unit 48. The first image data compression unit corresponds to the first image data compression unit 19 and the first image data compression unit 49. The second image data compression unit corresponds to the second image data compression unit 21 and the second image data compression unit 51. The image data storage unit corresponds to the first image data storage unit 22 and the third image data storage unit 52. The image transmission unit corresponds to the wireless transmitting unit 20, the first wireless transmitting unit 50, and the second wireless transmitting unit 38. The operating unit corresponds to the endoscope operating unit 11 and the endoscope operating unit 41. The image selection unit corresponds to the endoscope operating unit 11, the endoscope control unit 13, the endoscope operating unit 41, and the endoscope control unit 43.

It is also possible for a program which achieves the respective steps shown in FIG. 3, FIG. 4, FIG. 8, FIG. 9, and FIG. 10 to be recorded on a computer-readable recording medium. It is also possible for the processing executed by the communication terminal to be performed by causing this program recorded on a recording medium to be read and executed by a computer system. Note that, here, the term 'computer system' may include the OS (Operating System) and hardware such as peripheral devices and the like.

Moreover, if a WWW system is being utilized, then 'computer system' can also include a homepage provider environment (or display environment). Moreover, 'Computer readable recording medium' refers to a flexible disk, an electro-optic disk, ROM, recordable non-volatile memory such as flash memory, transportable media such as a CD-ROM and the like, and recording devices such as hard disks that are built into a computer system.

Moreover, 'Computer readable recording medium' also includes devices that hold a program for a fixed time such as the internal volatile memory (for example, DRAM (Dynamic random Access Memory)) in a computer system which forms the server or client when the program is transmitted via a network such as the Internet or via a communication line such as a telephone line.

Moreover, this program may also be transmitted from a computer system that stores the program on a storage device or the like via a transmission medium. Alternatively, this program may be transmitted to another computer system by means of a transmission wave within the transmission medium. Here, the 'transmission medium' which transmits the program refers to a medium having a function of transmitting information such as a network such as the Internet or a communication line such as a telephone line.

Moreover, the above described program may also be designed to fulfill a portion of the above described functions. Furthermore, the above described program may also achieve these functions in combination with a program which is already recorded on the computer system. The above described program may also be what is known as a differential file (i.e., a differential program).

INDUSTRIAL APPLICABILITY

According to the present invention, an image transmission terminal stores static image data that has a large data size in the image transmission terminal without wirelessly transmitting this data. As a result, a user is able to obtain static image data having a high image quality in an image transmission terminal. In addition, as a result of the image transmission terminal wirelessly transmitting the static image data having a large data size during blank periods of the moving image transmission, a user is able to obtain static image data having a high image quality on a display apparatus. Namely, the present invention makes it possible to achieve a superior image transmission terminal in order to wirelessly transmit image data.

DESCRIPTION OF THE REFERENCE NUMERALS

10 . . . Endoscope 11 . . . Endoscope operating unit 12 . . . Endoscope power supply 13 . . . Endoscope control unit 14 . . . Light control unit 15 . . . Light source unit 16 . . . Light emitting unit 17 . . . Image capture unit 18 . . . Image data generation unit 19 . . . First image data compression unit 20 . . . Wireless transmitting unit 21 . . . Second image data compression unit 22 . . . First image data storage unit Display apparatus 31 . . . Display apparatus operating unit 32 . . . Display apparatus power supply 33 . . . Display apparatus control unit 34 . . . Wireless receiving unit 35 . . . Image data expansion unit 36 . . . Image processing unit 37 . . . Display unit 38 . . . Second image data storage unit 39 . . . External interface 40 . . . Endoscope 41 . . . Endoscope operating unit 42 . . . Endoscope power supply 43 . . . Endoscope control unit 44 . . . Light control unit 45 . . . Light source unit 46 . . . Light emitting unit 47 . . . Image capture unit 48 . . . Image data generation unit 49 . . . First image data compression unit 50 . . . First wireless transmitting unit 51 . . . Second image data compression unit 52 . . . Third image data storage unit 53 . . . Second wireless transmitting unit 60 . . . Display apparatus 61 . . . Display apparatus operating unit 62 . . . Display apparatus power supply 63 . . . Display apparatus control unit 64 . . . First wireless receiving unit 65 . . . Image data expansion unit 66 . . . Image processing unit 67 . . . Display unit 68 . . . Second wireless receiving unit 69 . . . Fourth image data storage unit 70 . . . External interface

What is claimed is:

1. An image transmission terminal comprising:
   an operating unit;
   an image capture unit that outputs a pixel signal that corresponds to an amount of light irradiated onto an imaging element;
   an image data generating unit that generates and then outputs an image frame data based on the pixel signal;
   a first image data compression unit that compresses the image frame data at a predetermined compression rate and then outputs the image frame data;
   a second image data compression unit that, when receiving a command to keep the image frame data uncompressed or to compress the image frame data at a lower compression rate than the predetermined compression rate from the operating unit, outputs a non-compression image frame data which remains uncompressed or a low-compression image frame data in which the image frame data is compressed at a lower compression rate than the predetermined compression rate;
   an image data storage unit that stores the non-compression image frame data or the low-compression image frame data output from the second image data compression unit; and
   an image transmission unit that wirelessly transmits the image frame data stored in the image data storage unit and output from the second image data compression unit, wherein
   the image transmission unit configured to operate at least one of a first image transmission process that wirelessly transmits the image frame data output from the second image data compression unit and stored in the image data storage unit during a transmission blank period in wireless transmission of the image frame data continuously output from the first image data compression unit, or a second image transmission process that wirelessly transmits the image frame data output from the second image data compression unit and stored in the image data storage unit after receiving a stop command of wireless transmission of the image frame data continuously output from the first image data compression unit via the operating unit.

2. The image transmission terminal according to claim 1, wherein,
   when the image transmission unit operates the second image transmission process, the image transmission unit wirelessly transmits the image frame data output from the second image data compression unit and stored in the image data storage unit after performing a communication disconnection command operation by the operating unit.

3. The image transmission terminal according to claim 2, further comprising:
   a first transmitting unit wirelessly transmits the image frame data output from the first image data compression unit; and
   a second transmitting unit wirelessly transmits the image frame data output from the second image data compression unit.

4. The image transmission terminal according to claim 2, further comprising
   a control unit that, when receiving a command that either remains the image frame data uncompressed or compresses the image frame data at a lower compression rate than the predetermined compression rate from the operating unit, commands so as to attach a command information to the image frame data, the command information include a command for storing the image frame data being output from the first image frame data compression unit.

5. The image transmission terminal according to claim 1, further comprising
   a power supply, wherein
   when the image transmission unit operates the second image transmission process, the image transmission unit wirelessly transmits the image frame data output from the second image data compression unit and stored in the image data storage unit after performing a command to stop supplying power by the operating unit.

6. The image transmission terminal according to claim 1, wherein
   the image transmission terminal is an endoscope, and wherein
   when the image transmission unit operates the second image transmission process, the image transmission unit wirelessly transmits the image frame data output from the second image data compression unit and stored in the image data storage unit after receiving a command to end examination being performed with the endoscope.

7. The image transmission terminal according to claim 6, wherein
   when the image transmission unit operates the second image transmission process, the image transmission unit wirelessly transmits the image frame data output from the second image data compression unit and stored in the image data storage unit after performing a communication disconnection command operation by the operating unit.

8. The image transmission terminal according to claim 6, further comprising
a power supply, wherein
when the image transmission unit operates the second image transmission process, the image transmission unit wirelessly transmits the image frame data output from the second image data compression unit and stored in the image data storage unit after performing a command to stop supplying power by the operating unit.

9. The image transmission terminal according to claim 6, further comprising
a light control unit and a light emitting unit, wherein
when the image transmission unit operates the second image transmission process, the image transmission unit wirelessly transmits the image frame data output from the second image data compression unit and stored in the image data storage unit after performing a command to stop controlling a light to the light control unit, or a command to turn off a light to the light emitting unit by the operating unit.

10. An image transmission method comprising steps of:
outputting a pixel signal that corresponds to an amount of light irradiated onto an imaging element;
generating an image frame data and then outputting the image frame data based on the pixel signal;
compressing the image frame data at a predetermined compression rate and then outputting the image frame data;
outputting a non-compression image frame data which remains the image frame data uncompressed or a low-compression image frame data in which the image frame data is compressed at a lower compression rate than the predetermined compression rate, when receiving a command to keep the image frame data uncompressed or to compress the image frame data at a lower compression rate than the predetermined compression rate;
storing the non-compression image frame data or the low-compression image frame data; and
wirelessly transmitting the image frame data stored as the non-compression image frame data or the low-compression image frame data, wherein
in the step of wirelessly transmitting the image frame data, at least one of
a first image transmission process that wirelessly transmits the image frame data stored as the non-compression image frame data or the low-compression image frame data during a transmission blank period in wirelessly transmission of the image frame data compressed at the predetermined compression rate and continuously output, or
a second image transmission process that wirelessly transmits the image frame data stored as the non-compression image frame data or the low-compression image frame data after receiving a stop command of wireless transmission of the image frame data compressed at the predetermined compression rate and continuously output, is performed.

11. A non-transitory computer readable medium recorded with a program for causing a computer to execute steps of:
outputting a pixel signal that corresponds to an amount of light irradiated onto an imaging element;
generating an image data and then outputting the image frame data based on the pixel signal;
compressing the image frame data at a predetermined compression rate and then outputting the image frame data;
outputting a non-compression image frame data which remains the image frame data uncompressed or a low-compression image frame data in which the image frame data is compressed at a lower compression rate than the predetermined compression rate, when receiving a command to keep the image frame data uncompressed or to compress the image frame data at a lower compression rate than the predetermined compression rate;
storing the non-compression image frame data or the low-compression image frame data; and
wirelessly transmitting the image frame data stored as the non-compression image frame data or the low-compression image frame data, wherein
in the step of wirelessly transmitting the image frame data, at least one of
a first image transmission process that wirelessly transmits the image frame data stored as the non-compression image frame data or the low-compression image frame data during a transmission blank period in wirelessly transmission of the image frame data compressed at the predetermined compression rate and continuously output, or
a second image transmission process that wirelessly transmits the image frame data stored as the non-compression image frame data or the low-compression image frame data after receiving a stop command of wireless transmission of the image frame data compressed at the predetermined compression rate and continuously output,
is performed.

* * * * *